United States Patent

Darms et al.

[11] Patent Number: 4,649,181
[45] Date of Patent: Mar. 10, 1987

[54] GLYCIDYLOXY DIKETONES

[75] Inventors: Roland Darms, Therwil; Charles E. Monnier, Villars-sur-Glâne, both of Switzerland

[73] Assignee: Ciba-Geigy Corporation, Ardsley, N.Y.

[21] Appl. No.: 718,575

[22] Filed: Apr. 1, 1985

[30] Foreign Application Priority Data

Apr. 4, 1984 [CH] Switzerland .......................... 1693/84

[51] Int. Cl.⁴ ........................................... C08F 283/00
[52] U.S. Cl. .................................. 525/524; 528/220; 549/551; 549/556
[58] Field of Search ............... 549/556, 551; 525/524; 528/220

[56] References Cited

U.S. PATENT DOCUMENTS

| | | | |
|---|---|---|---|
| 2,922,777 | 1/1960 | Burgert et al. | 524/109 |
| 3,522,210 | 7/1970 | Sellers et al. | 549/556 |
| 3,821,310 | 6/1974 | Brunetti et al. | 568/330 |
| 4,111,907 | 9/1978 | Green et al. | 549/556 |
| 4,276,226 | 6/1981 | Clement et al. | 260/410.5 |
| 4,308,195 | 12/1981 | Mayer et al. | 549/556 |
| 4,549,008 | 10/1985 | Renner et al. | 528/220 |
| 4,565,859 | 1/1986 | Murai et al. | 549/551 |

FOREIGN PATENT DOCUMENTS 47-42749 10/1972 Japan .

OTHER PUBLICATIONS

A. L. Cupples et al, Advan. Chem. Ser. 92, 173 (1970).
E. S. Dzhavadyan et al, Polymer Bull. 4, 479 (1981).

Primary Examiner—Lucille M. Phynes
Attorney, Agent, or Firm—Luther A. R. Hall

[57] ABSTRACT

Novel glycidyloxy diketones of the formula I

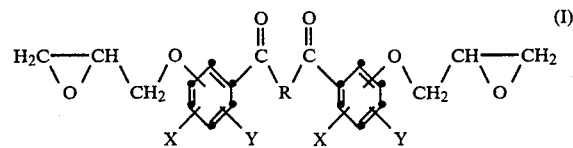

(in which, for example, X is glycidyloxy, Y is H and R is 1,3-phenylene) are described.

The compounds of the formula can be used together with customary curing agents and/or curing catalysts for the preparation of crosslinked (cured) products which have good thermal and mechanical properties.

16 Claims, No Drawings

GLYCIDYLOXY DIKETONES

The present invention relates to novel di-, tri- or wherein X is hydrogen, alkyl, alkoxy or glycidyloxy; Y is hydrogen or alkyl, and R is a direct bond, alkylene, alkenylene or phenylene products.

Epoxide resins are used in numerous fields, for example as adhesives, lacquers, compression moulding materials, insulators and composite materials, and a large number of chemically different epoxide resins are available commercially. The epoxide resins generally used are glycidyl derivatives derived from a bisphenol, a dicarboxylic acid or a diamine and epichlorohydrin.

Glycidyloxy-substituted benzophenones and the use thereof as epoxide resins are also known; cf., for example, A. L. Cupples et al. [Advan. Chem. Ser. 92, 173-207 (1970)] and E. S. Dzhavadyan et al. [Polymer Bulletin 4, 479-485 (1981)].

It is also known from US Patent Specification 2,922,777 that, inter alia, ortho-hydroxyglycidyloxybenzophenones and 1,3-bis-(4'-glycidyloxy-2'-hydroxybenzoyl)benzene can be employed as light stabilisers or heat stabilisers for polyolefines.

The invention relates to novel glycidyloxy diketones of the formula I

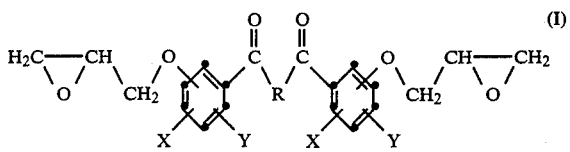

in which the substitutents X independently of one another are hydrogen, alkyl having 1 to 6 C atoms, glycidyloxy or alkoxy having 1 to 6 C atoms, the substituents Y independently of one another are hydrogen or alkyl having 1 to 6 C atoms and R is a direct bond, a group of the formula $-C_mH_{2m}-$, $-C_nH_{2n-2}-$ or $-C_nH_{2n-4}-$ in which $m=1-12$ and $n=2-12$, a divalent, saturated or unsaturated cycloaliphatic radical having up to 14 C atoms, a divalent araliphatic radical having up to 14 C atoms, a divalent $C_6-C_{12}$ aromatic radical or a group of the formula II

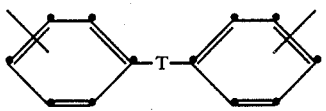

in which T is a direct bond, methylene, isopropylidene, O, S, NH, CO or $SO_2$.

The compounds of the formula I can be obtained, for example, by converting a compound of the formula III

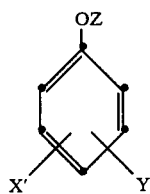

or a mixture of various compounds of the formula III in which Z is hydrogen or alkyl having 1 to 6 C atoms and X' is hydrogen, alkyl having 1 to 6 C atoms, hydroxyl or alkoxy having 1 to 6 C atoms and Y is as defined above, in the presence of a Friedel-Crafts catalyst and by means of a compound of the formula IV

$$CL-CO-R-CO-Cl \qquad (IV),$$

in which R is as defined above, into a compound of the formula V

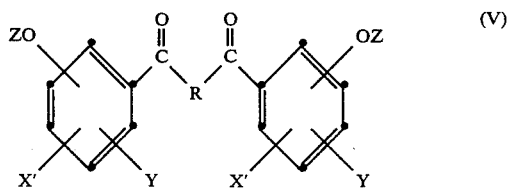

if desired, O-dealkylating the compounds of the formula V (i.e. converting them into a compound of the formula V in which Z=H and X'=H, alkyl having 1 to 6 C atoms or hydroxyl) and then reacting the product with an epihalogenohydrin. An O-alkylation with a $C_1-C_6$ alkyl halide can, if desired, be carried out before or after the reaction with the epihalogenhydrin.

Alkyl substitutents X and Y having 1 to 6 C atoms can be linear or branched. Examples of suitable substituents are methyl, ethyl, n-propyl and isopropyl and the various butyl, pentyl and hexyl isomers. The same applies to the corresponding O-alkyl radicals of the alkoxy substituents which have 1 to 6 C atoms. In general, linear alkyl or alkoxy radicals are preferred, particularly methyl, ethyl, methoxy and ethoxy.

The bridge members R of the formulae $-C_mH_{2m}-$, $-C_nH_{2n-2}-$ and $-C_nH_{2n-4}-$ can be linear and branched divalent alkylene, alkenylene, alkadienylene or alkynylene radicals, for example 1,4-, 1,3- or 1,2-butylene, 1,6-hexylene or 1,3-hexylene, 1,8-, 2,7- or 3,6-octylene, 1,2-ethenylene, 1,4-but-2-enylene, 1,6-hexa-2,4-dienylene and 1,6-hex-3-inylene.

The following may be mentioned as examples of saturated or unsaturated cycloaliphatic divalent radicals R: 1,2-cyclopentylene or 1,3-cyclopentylene, 1,2-, 1,3- or 1,4-cyclohexylene, 1,2-, 1,3-, 1,4-, 3,4- and 3,5-cyclopentenylene, the 4,4'-bis-(cyclohexylene)-methane radical and the dimethylenecylohexane radical, 1,2-cyclohexenylene and 3,6-cyclohexenylene.

Examples of divalent araliphatic radicals R are the dimethylenebenzene, dimethylenetoluene and dimethylenenaphthalene radicals.

Examples of divalent aromatic radicals R having 6 to 12 C atoms are 1,2-, 1,3 or 1,4-phenylene groups, toluylene groups and naphthylene groups, such as the 2,6-, 1,4- and 1,5-naphthylene group.

The invention also relates to compounds of the formula V in which R, Z, Y and X' are as defined above, in so far as they are novel.

Preferred compounds of the formula I are those in which the substitutents X and the substituents Y are in each case identical, the substituents X and Y and the glycidyl groups are each in the same position in relation to the carbonyl group and R is a group of the formula $-C_mH_{2m}-$ in which m is 1 or 8, or is phenylene.

Compound of the formula I which are particularly preferred are those in which the substituents X are each hydrogen, alkyl having 1 to 4 C atoms or alkoxy having 1-4 C atoms, and the substituents Y are each hydrogen or alkyl having 1 to 4 C atoms, and the glycidyloxy groups are each attached in the para-position relative to the carbonyl groups.

Compounds of the formula I which are very particularly preferred are those in which the substituents X and Y are each identical and are methyl or, in particular, hydrogen and R is 1,4-phenylene, 1,3-phenylene, 1,4-butylene or 1,8-octylene.

Compounds of the formula I which are also preferred are those in which each of the substituents X is a glycidyloxy group and each of the substituents Y is hydrogen or an alkyl group having 1 to 4 C atoms, and the glycidyloxy groups are each attached in the ortho-position and the para-position in relation to the carbonyl groups. Amongst these, particularly preferred compounds are those in which each of the substituents Y is hydrogen and R represents 1,4-butylene and, in particular, 1,3-phenylene or 1,4-phenylene.

The starting materials of the formulae III and IV are known per se or can be prepared in a manner known per se.

The preparation of the compounds of the formula V, i.e. the intermediates produced in the synthesis of the compounds, according to the invention, of the formula I, can be carried out analogously to the processes described in U.S. Pat. Nos. 3,821,310 and 4,276,226.

In the Friedel-Crafts reaction of the compounds of formula III with the dicarboxylic acid dichlorides of the formula IV, it is possible to convert alkoxy groups OZ and/or X' into hydroxyl groups, especially if they are in the orthoposition in relation to the carbonyl group in the reaction product of the formula V. If desired, any alkoxy groups still present can subsequently be dealkylated by further heating in the presence of the Friedel-Crafts catalyst.

The end products, according to the invention, of the formula I are finally obtained by reacting compounds of the formula V with an epihalogenohydrin, preferably epichlorohydrin, in the presence of a base and, if appropriate, a catalyst. Compounds of the formula V in which OZ and/or X' are a hydroxyl group are reacted with $C_1$–$C_6$-alkylhalides in order to introduce alkoxy groups, before or after the reaction with the epihalogenohydrin. The particular sequence of reactions here depends on the product desired. If the two substituents OZ and X' of the compound V are hydroxyl groups, the first alkylation or glycidylation generally takes place on the OH in the para-position or meta-position relative to the carbonyl group, and the second alkylation or glycidylation takes place on the OH in the ortho-position relative to the carbonyl group.

Aluminium trichloride is an example of a Friedel-Crafts catalyst which can be used for the reaction of compounds of the formulae III and IV and for the possible dealkylation.

The dealkylation or alkylation of compounds of the formula V can be carried out as described in U.S. Pat. No. 3,821,310.

The glycidylation of compounds of the formula V is carried out in a manner known per se by reacting these compounds in the presence of a base, for example sodium hydroxide, and, if appropriate, a catalyst, for example tetramethylammonium chloride, at an elevated temperature (approx. 50°–150° C.) with an epihalogenohydrin, especially epichlorohydrin.

The compounds, according to the invention, of the formula I can be isolated and purified in a customary manner, for example by extraction or recrystallisation from suitable solvents, for example acetone or methylcellosolve/water, or by filtration over silica gel using suitable solvents, for example toluene/ethanol.

The compounds, according to the invention, of the formula I are suitable for use as epoxide resins for the preparation of crosslinked products.

The present application also relates, therefore, to curable mixtures which are suitable, for example, for the production of shaped articles, impregnations, coatings, adhesive bonds and especially composite materials, matrix resins or sintered powder lacquers. They contain: (a) a compound of the formula I and (b) a curing agent and/or a curing catalyst for epoxide resins.

Examples of curing agents which may be mentioned are the customary curing agents for epoxide resins, including aliphatic, cycloaliphatic, aromatic and heterocyclic amines, such as bis-(4-aminophenyl)-methane, aniline-formaldehyde resins, bis-(4-aminophenyl)sulfone, propane-1,3-diamine, hexamethylenediamine, diethylenetriamine, triethylenetetramine, 2,2,4-trimethylhexane-1,6-diamine, m-xylylenediamine, bis-(4-aminocyclohexyl)-methane, 2,2-bis-(4-aminocyclohexyl)-propane and 3-aminomethyl-3,5,5-trimethylcyclohexylamine (isophorondiamine), polyaminoamides, for example those formed from aliphatic polyamines and dimerised or trimerised fatty acids, polyphenols, such as resorcinol, hydroquinone, 2,2-bis-(4-hydroxyphenyl)-propane and phenol/aldehyde resins, polythiols, such as the polythiols obtainable commercially under the name "Thiokoles", polycarboxylic acids and anhydrides thereof, for example phthalic anhydride, tetrahydrophthalic anhydride, hexahydrophthalic anhydride, hexachloroendomethylenetetrahydrophthalic anhydride, pyromellitic dianhydride or benzophenone-3,3,4',4'-tetracarboxylic dianhydride, the acids of the aforementioned anhydrides and also isophthalic acid and terephthalic acid. It is also possible to use curing agents having a catalytic action, for example tin salts of alkanoic acids (for example tin octanoate), Friedel-Crafts catalysts, such as boron trifluoride and boron trichloride and complexes and chelate compounds thereof obtained by reacting boron trifluoride with, for example, 1,3-diketones.

The amount of curing agent employed depends on the chemical nature of the curing agent and on the properties desired in the curable mixture and the cured product. The maximum amount can be determined readily. If the curing agent is an amine, 0.75 to 1.25 equivalents of amine hydrogen are normally employed per 1 epoxide equivalent. If polycarboxylic acids or their anhydrides are employed, 0.4 to 1.1 equivalents of carboxyl group or anhydride group are generally used per 1 equivalent of epoxide group. If polyphenols are used as curing agents, it is preferable to employ 0.75 to 1.25 phenolic hydroxyl groups per 1 epoxide equivalent.

Curing agents having a catalytic action are generally employed in amounts of 1 to 40 parts by weight per 100 parts by weight of epoxide resin.

If desired, active thinners, for example styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary, aliphatic monocarboxylic acids, can be added to the curable mixtures in order to reduce their viscosity.

It is also possible to employ curing accelerators in the curing reaction; examples of such accelerators are tertiary amines, salts thereof or quaternary ammonium compounds, for example benzyldimethylamine, 2,4,6-tris-(dimethylaminomethyl)-phenol, 1-methylimidazole, 2-ethyl-4-methylimidazole, 4-aminopyridine or tripentylammonium phenolate; or alkali metal alcoholates, for example Na alcoholates of 2,4-dihydroxy-3-hydroxymethylpentane. The curing of mixtures according to the invention is preferably carried out within the temperature range from 50° C. to 300° C., preferably 80° to 250° C.

The curing can also be carried out in an known manner in 2 or more stages, the first curing stage being carried out at a low temperature and the subsequent curing at a higher temperature.

If desired, the curing can also be carried out in 2 stages by first prematurely discontinuing the curing reaction or by carrying out the first stage at a rather low temperature, whereby a curable precondensate which is still fusible and/or soluble (the so-called "B-stage") is obtained from the epoxy component (a) and the curing agent (b). A precondensate of this type can be used, for example, for the preparation of "prepregs", compression moulding materials or sintered powders.

The term "curing", as used here, denotes the conversion of the soluble, either liquid or fusible, polyepoxides into solid, insoluble and infusible, three-dimensionally crosslinked products or materials, as a rule with simultaneous shaping to give shaped articles, such as castings, mouldings and laminates, impregnations, coatings, films or adhesive bonds.

The present curable mixtures can also contain suitable plasticisers, such as dibutylphthalate, dioctylphthalate or tricresylphthalate.

Finally, the curable mixtures can be treated, before curing, in any phase with diluent, fillers and reinforcing agents, for example coal-tar, bitumen, textile fibres, glass fibres, asbestos fibres, boron fibres, carbon fibres, mineral silicates, mica, powdered quartz, hydrated aluminium oxide, bentonites, kaolin, silica aerogel or metal powders, for example aluminium powder or iron powder, an also pigments and dyes, such as carbon black, oxide colourant, titanium dioxide and others. It is also possible to add other customary additives, for example fire-retarding agents, such as antimony trioxide, thixotropic agents or flow control agents such as silicones, waxes or stearates (some of which can also be used as mould release agents), to the curable mixtures.

The preparation of the present curable mixtures can be effected in a customary manner using known mixing units (stirrers, kneaders, rolls ets.).

The present curable epoxide resin mixtures are used, in particular, in the fields of surface protection, electrical engineering, laminating processes and building. They can be used in a formulation adapted to suit in each case the particular end use, in an unfilled or filled state, as paints, lacquers, such as sintered powder lacquers, as compression moulding materials, dipping resins, casting resins, injection moulding formulations, impregnating resins and adhesives, tool resins, laminating resins, sealing compounds, knifing fillers, flooring materials and binders for mineral aggregates.

The cured products prepared by means of the compounds, according to the invention, of the formula I are distinguished by very good thermal and mechanical properties. For example, they have a high dimensional stability under heat and a high resistance to heat, while having at the same time a high flexural strength and tensile shear strength. These excellent properties are not essentially impaired even after prolonged storage in water. The cured products are also distinguished by very good resistance to chemicals.

High dimensional stability under heat and flexural strength are particularly pronounced in the case of aliphatic and, especially, aromatic tetraglycidyloxy diketones of the formula I, whereas corresponding aromatic and, especially, aliphatic diglycidyloxy diketones of the formula I are particularly distinguished by high tensile shear strength.

The choice of suitable compounds according to the invention depends on the properties desired in the cured products and on the specific uses.

The preparation, and the properties and use, of the compounds according to the invention are described in the following examples.

PREPARATION EXAMPLES

EXAMPLE 1

4,4'-diglycidyloxybenzil

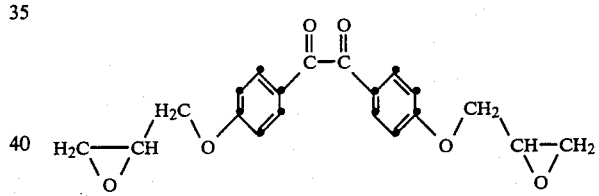

6.0 g (0.0248 mole) of 4,4'-dihydroxybenzil, 34.8 g (0.3752 mole) of epichlorohydrin and 0.47 g of 50% aqueous tetramethylammonium chloride solution are initially placed in a 200 ml sulfonation flask equipped with a thermometer, a condenser, a dropping funnel, a stirrer and a water separator, and are heated to 105°–110° C. After a reaction time of 4 hours, the reaction product is cooled to 60° C. and 4.74 g (0.059 mole) of 50% aqueous sodium hydroxide solution are added dropwise with simultaneous removal of water from the system. The precipitated sodium chloride is filtered off and washed with chloroform, and the filtrate is concentrated. Recrystallisation from acetone gives 5.70 g (64.92% of theory) of 4,4'-diglycidyloxybenzil of melting point 120°–130° C.

IR (KBr): 3,400, 2,940, 1,640, 1,610 and 1,250 cm$^{-1}$.

NMR (CDCl$_3$): 2.6–3.0 m, 4H (CH$_2$—CH—); 3.2–3.5 m 2H (CH—CH$_2$); 3.8–4.5 m, 4H (—OCH$_2$—); 6.8–7.7 dd, 8H (arom H).

Epoxide content (titration with 0.1N HClO$_4$): 4.71 mole/kg (83.58% of theory).

EXAMPLE 2

1,4-bis-(4'-glycidyloxybenzoyl)-benzene

EXAMPLE 4

1,4-bis-(4'-glycidyloxy-3',5'-dimethylbenzoyl)-benzene

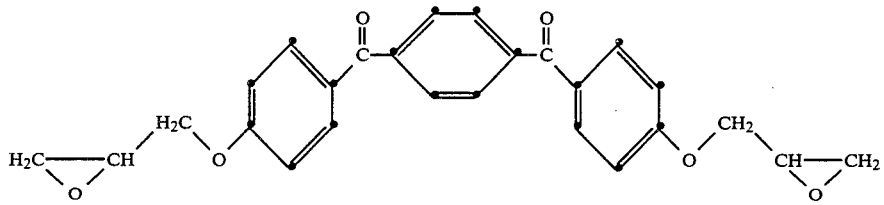

5.0 g (0.0157 mole) of 1,4-bis-(4'-hydroxybenzoyl)-benzene, 22.0 g (0.236 mole) of epichlorohydrin and 0.3 g of 50% aqueous tetramethylammonium chloride solution are initially placed in a 200 ml sulfonation flask equipped with a stirrer, a thermometer, a condenser and a water separator, and are heated at 105°–110° C. for 4 hours. After cooling to 60° C., 3.0 g of 50% aqueous sodium hydroxide solution are added dropwise with simultaneous removal of water. The reaction mixture is filtered, and the filtrate is concentrated in vacuuo, whereupon 1,4-bis-(4'-glycidyloxybenzoyl)-benzene crystallises out. After drying, 3.14 g (46.4% of theory) of slightly beige 1,4-bis-(4'-glycidyloxybenzoyl)-benzene of melting point 199°–201° C. are obtained.

IR (KBr): 1,650, 1,600, 1,500, 1,400 and 1,250 $cm^{-1}$.

Epoxide content (titration with 0.1N $HClO_4$): 4.646 mole/kg (93.86% of theory).

EXAMPLE 3

1,3-bis-(4'-glycidyloxybenzoyl)-benzene 10.0 g (0.0314 mole) of 1,3-bis-(4'-hydroxybenzoyl)-benzene, 44.0 g (0.475 mole) of epichlorohydrin and 0.6 g of 50% aqueous tetramethylammonium chloride solution are initially placed in a 200 ml sulfonation flask equipped with a stirrer, a condenser, a thermometer and a water separator, and are heated at 110° C. After a reaction time of 4 hours, the reaction mixture is cooled to 60° C. and 6.0 g (0.075 mole) of 50% aqueous sodium hydroxide solution are added dropwise, sodium chloride being precipitated in solid form. When the removal of water is complete, the reaction mixture is filtered and the filtrate is taken up in epichlorohydrin, washed with water, dried over sodium sulphate, filtered and concentrated in vacuo. This gives 13.10 g (97% of theory) of a viscous resin which crystallises out on being left to stand. The crude product is recrystallised from methylcellosolve/water, and, after drying, 9.38 g (69.43% of theory) of 1,3-bis-(4'-glycidyloxybenzoyl)-benzene of melting point 88°–93° C. are isolated in the form of virtually colourless needles.

IR (KBr): 1,650, 1,600 and 1,250 $cm^{-1}$.

NMR ($CDCl_3$): 2.5–3.1 m 4H ($CH_2$—CH—); 3.3–3.6 m 2H (CH—$CH_2$); 4.0–4.5 m 4H (—$OCH_2$—); 6.8–8.0 m 12H (arom.H).

Epoxide content (titration with 0.1N $HClO_4$): 4.26 mole/kg (91.69% of theory).

13.10 g (0.035 mole) of 1,4-bis-(4'-hydroxy-3',5'-dimethylbenzoyl)-benzene, 49.0 g (0.52 mole) of epichlorohydrin and 0.5 g of 50% aqueous tetramethylammonium chloride solution are heated at 105°–110° C. in a 200 ml sulfonation flask equipped with a stirrer, a condenser, a thermometer and a water separator. After a reaction time of 4 hours, the reaction mixture is cooled to 60° C. and 12.8 g (0.16 mole) of 50% aqueous sodium hydroxide solution are added dropwise, with simultaneous removal of water from the system. The precipitated sodium chloride is filtered off and the filtrate is washed with epichlorohydrin and concentrated in vacuo. The residue (15.0 g) is recrystallised from 50 ml of toluene, filtered off and dried. This gives 11.5 g (67.5% of theory) of 1,4-bis-(4'-glycidyloxy-3',5'-dimethylbenzoyl)benzene of melting point 164°–170° C. in the form of a virtually colourless powder.

IR (KBr): 2,920, 1,640, 1,590, 1,320, 1,210, 1,130 and 1,000 $cm^{-1}$.

NMR ($CDCl_3$): 2.33 s 12H (—$CH_3$); 2.6–3.0 m 4H (—$CH_2$—CH—); 3.2–3.6 m 2H (—CH—$CH_2$—); 3.6–4.3 m 4H (O—$CH_2$—); 7.0–7.9 m 8H (arom.H).

Epoxide content (titration with 0.1 $HClO_4$): 3.91 mole/kg (95.03% of theory).

Elementary analysis: $C_{30}H_{30}O_6$ (486.56); calculated C 74.06%; H 6.22%; found C 74.16%; H 6.32%.

EXAMPLE 5

1,4-bis-(4'-glycidyloxybenzoyl)-butane

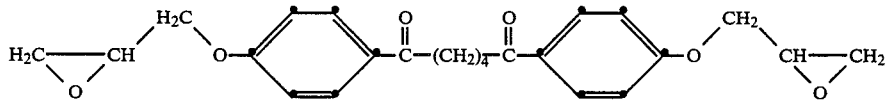

16.41 g (0.055 mole) of 1,4-bis-(4'-hydroxybenzoyl)-butane, 77.07 g (0.832 mole) of epichlorohydrin and 1.05 g of 50% aqueous tetramethylammonium chloride solution are suspended in a 350 ml sulfonation flask equipped with a stirrer, a thermometer, a condenser, a dropping funnel and a water separator. The mixture is heated under reflux (112°–116° C.) for 4 hours; the reaction product is then cooled to 60° C., and the water is removed azeotropically at 40° C. in the course of approx. 2.5 hours, while 10.51 g (0.131 mole) of aqueous sodium hydroxide solution is slowly added dropwise. The reaction mixture is stirred at this temperature for about a further 16 hours and is then transferred to a separating funnel, washed several times with water, dried and concentrated, whereupon a semi-crystalline product is isolated. 11.00 g (48.72% of theory) of 1,4-bis-(4'-glycidyloxybenzoyl)-butane of melting point 126°–130° C. are obtained after recrystallisation from acetone.

IR (KBr): 3,500–3,300, 3,100–2,940, 1,670, 1,600, 1,510, 1,360, 1,260, 1,170, 1,030, 970, 920 and 830 cm$^{-1}$.

NMR (d$_6$-DMSO): 1.5–1.8 m 4H (CH$_2$-aliph.); 2.4–4.6 m 14H (—CH$_2$CO— and glycidyl-H); 6.8–7.8 dd (J=8 Hz), (arom H).

Epoxide content (titration with 0.1N HClO$_4$): 4.835 mole/kg (99.25% of theory).

EXAMPLE 6

1,8-bis-(4'-glycidyloxybenzoyl)-octane 17.72 g (0.05 mole) of 1,8-bis-(4'-hydroxybenzoyl)-octane, 70.03 g (0.756 mole) of epichlorohydrin and 0.96 g of 50% aqueous tetramethylammonium chloride solution are initially placed in a 200 ml sulfonation flask equipped with a condenser, a thermometer, a stirrer, a dropping funnel and a water separator, and are heated at 105°–110° C. After 4 hours, the reaction mixture is cooled to 60° C. and 9.55 g (0.118 mole) of 50% aqueous sodium hydroxide solution are added dropwise with simultaneous removal of water. The reaction mixture is taken up in epichlorohydrin, washed with water, dried and concentrated. This gives 21.73 g (93.14% of theory) of colourless 1,8-bis-(4'-glycidyloxybenzoyl)-octane of melting point 118°–119° C.

IR (KBr): 3,500, 2,920, 2,840, 1,680, 1,600 and 1,230 cm$^{-1}$.

NMR (CDCl$_3$): 1.0–2.0 m 12H (—CH$_2$)6, 2.7–3.0 m 8H

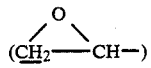

and

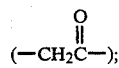

3.0–3.5 m 2H (—CH—CH$_2$); 3.7–4.5 m 4H (CH$_2$O); 6.7–7.8 dd 8H (arom.H).

Epoxide content (titration with 0.1N HClO$_4$): 3.988 mole/kg (93.03% of theory).

EXAMPLE 7

1,4-bis-(2',4'-diglycidyloxybenzoyl)-benzene

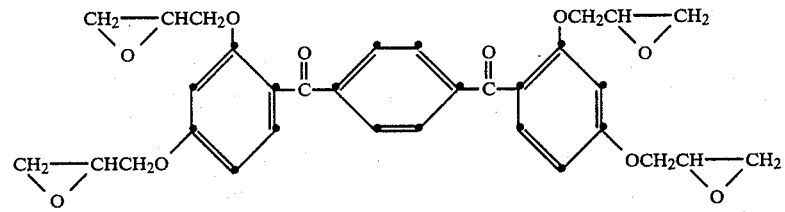

8.0 g (0.0228 mole) of 1,4-bis-(2',4'-dihydroxybenzoyl)-benzene, 31.7 g (0.343 mole) of epichlorohydrin and 0.4 g of 50% aqueous tetramethylammonium chloride solution are initially placed in a 200 ml sulfonation flask equipped with a stirrer, a condenser, a thermometer and a water separator and are heated at 105°–110° C. for 4 hours. The reaction mixture is then cooled to 60° C. and 8.3 g (0.104 mole) of 50% aqueous sodium hydroxide solution are added dropwise with simultaneous removal of water from the system. The residue is taken up in epichlorohydrin, the precipitated sodium chloride is filtered off, and the filtrate is concentrated in vacuo. This gives 14.7 g of a brown oil which is filtered over silica gel (90:10 toluene:ethanol), whereupon 3.22 g (24.6% of theory) of 1,4-bis-(2',4'-diglycidyloxybenzoyl)-benzene of melting point 128°–133° C. are obtained.

IR (KBr): 3,060, 2,860, 1,640, 1,600 and 1,250 cm$^{-1}$.

NMR (d$_6$-DMSO): 2.4–2.6 m 8H (CH$_2$CH—); 2.8–3.1 m 4H (—CH—CH$_2$); 3.7–4.5 m 8H (—OCH$_2$); 6.6–7.8 m 10H (arom.H).

Epoxide content (titration with 0.1N HClO$_4$): 5.81 mole/kg (83.5% of theory).

EXAMPLE 8

1,3-bis-(2',4'-diglycidyloxybenzoyl)-benzene 150 g (0.427 mole) of 1,3-bis-(2',4'-dihydroxybenzoyl)-benzene, 59.4 g (0.642 mole) of epichlorohydrin and 8.0 g of 50% aqueus tetramethylammonium chloride solution are initially placed in a 1.5 l sulfonation flask equipped with a stirrer, a condenser, a thermometer and a water separator, and are heated at 105°–110° C. After a reaction time of 4 hours the reaction mixture is cooled to 60° C. and 155.8 g (1.95 moles) of 50% aqueous sodium hydroxide solution are added dropwise, with simultaneous removal of water from the system, finely divided sodium chloride being precipitated. The reaction mixture is filtered and the filtrate is washed with water, dried over Na$_2$SO$_4$ and concentrated in vacuo. This gives 242.7 g (98.9% of theory) of 1,3-bis-(2',4'-diglycidyloxybenzoyl)-benzene as an orange, viscous oil.

IR (KBr): 3,000, 2,860, 1,650, 1,600 and 1,250 cm$^{-1}$.

NMR (CDCl$_3$): 2.5–3.0 m 8H (—CH$_2$—CH—); 3.2–3.5 m 4H (—CH$_2$—CH—); 3.5–4.3 m 8H (—O—CH$_2$—); 6.5–7.8 m 10H (arom.H).

Epoxide content (titration with 0.1N HClO$_4$): 5.589 mole/kg (80.3% of theory).

EXAMPLE 9

1,4-bis-(2',4'-diglycidyloxybenzoyl)-butane 18.16 g (0.055 mole) of 1,4-bis-(2',4'-dihydroxybenzoyl)-butane, 86.84 g (0.938 mole) of epichlorohydrin and 0.97 g of 50% aqueous tetramethylammonium chloride solution are initially placed in a 350 ml sulfonation flask equipped with a stirrer, a thermometer, a condenser, a dropping funnel and a water separator, and are heated at 105°–110° C. After a reaction time of 4 hours the reaction mixture is cooled to 60° C.; 20.21 g (0.253 mole) of 50% aqueous sodium hydroxide solution are then added with simultaneous removal of water from the system. The resulting suspension is treated with water, and the organic phase is washed with water, dried over sodium sulphate and concentrated. This gives 28.62 g (93.84% of theory) of a red, viscous resin.

IR (film): 3,500, 3,030, 3,000, 2,820, 1,660 and 1,250 cm$^{-1}$.

NMR (d$_6$-DMSO): 1.2–1.6 s br 4H (—CH$_2$— aliph.); 2.0–4.5 m 24H (glycidyl-H and —CH$_2$CO—); 6.5–7.3 m 6H (arom.H).

Epoxide content (titration with 0.1N HClO$_4$): 5.307 mole/kg (73.58% of theory).

USE EXAMPLES

EXAMPLE I–VIII

Portions of 100 parts by weight of the corresponding glycidyloxy diketone are mixed with the amount indicated in Table 1 of bis-(4-aminophenyl)-methane, as curing agent. The reactivity of these mixtures is determined by means of the gel time and by means of differential thermoanalysis (DTA) on the one hand, and, on the other hand, the glass transition temperature (T$_g$) and the tensile shear strength of the cured products are measured.

The following compounds ae used in the examples:

I: 1,4-bis-(4'-glycidyloxybenzoyl)-benzene, (according to Example 2).

II: 1,3-bis-(4'-glycidyloxybenzoyl)-benzene, (according to Example 3).

III: 1,4-bis-(4'-glycidyloxy-3',5'-dimethylbenzoyl)-benzene, (according to Example 4).

IV: 1,4-bis-(4'-glycidyloxybenzoyl)-butane, (according to Example 5).

V: 1,8-bis-(4'-glycidyloxybenzoyl)-octane, (according to Example 6).

VI: 1,4-bis-(2',4'-diglycidyloxybenzoyl)-benzene, (according to Example 7).

VII: 1,3-bis-(2',4'-diglycidyloxybenzoyl)-benzene, (according to Example 8).

VIII: 1,4-bis-(2',4'-diglycidyloxybenzoyl)-butane, (according to Example 9).

poorer test values, "1", in 5N H$_2$SO$_4$ and/or in acetone and in chlorobenzene, respectively.

EXAMPLE IX 100 parts by weight of 1,3-bis-(2',4'-diglycidyloxybenzoyl)-benzene (prepared in accordance with Example 8) are mixed with 27.7 parts by weight of bis-(4-aminophenyl)-methane and are cured: (A) for 4 hours at 100° C. and 8 hours at 140° C., or (B) for 4 hours at 100° C., 8 hours at 140° C. and 6 hours at 180° C. The following properties are measured:

|  | A | B |  |
|---|---|---|---|
| impact strength (VSM 77,105) | 17 | 12 | kJ/m$^2$ |
| flexural strength (ISO 178) | 180 | 154 | N/mm$^2$ |
| strain of the outer fibre (ISO 178) | 6.9 | 4.1 | % |
| glass transition temperature | 174 | 202 | °C. |
| heat distortion point (ISO 75) | 163 | 192 | °C. |
| water absorption |  |  |  |
| after 4 days at 25° C. | 0.41 | 0.40 | % by weight |
| 1 hour, boiling water | 0.42 | 0.34 | % by weight |
| 100 hours boiling water | 5.2 | 5.9 | % by weight |
| dissipation factor, tanδ |  |  |  |
| (DIN 53,483) >1% above | 55 | 40 | °C. |
| >5% above | 104 | 90 | °C. |
| dielectric constant 23° C. (DIN 53,483) | 4.9 | 4.7 |  |
| volume resistivity at 23° C. (DIN 53,482) | 2.3 × 10$^{15}$ | 1.9 × 10$^{15}$ | Ohm cm |

EXAMPLE X 100 parts by weight of 1,3-bis-(2',4'-diglycidyloxybenzoyl)-benzene (prepared in accordance with Example 8) are mixed with 33.1 parts by weight of bis-(4-aminophenyl)-sulphone, and the following properties are measured on the mixture: Differential scanning calo-

TABLE 1

| Example | I | II | III | IV | V | VI | VII | VIII |
|---|---|---|---|---|---|---|---|---|
| curing agent (parts by weight) | 21.6 | 21.1 | 19.4 | 24.0 | 19.8 | 28.8 | 25.6 | 26.3 |
| gel time 140° C. | not melted | 5'55" | 19' | 5'20" | 10' | 2' | 1'50" | 1'15" |
| 160° C. | 3'10" | 4'35" | 18'40" | 4'15" | 6'15" | 1'25" | 1'25" | 1'05" |
| 180° C. | 55" | 1'15" | 4'50" | 1'15" | 7'50" | 30" | 30" | 20" |
| DTA$^f$ m.p. (°C.) | 91 | 60 + 74 | — | 81 + 117 | 81 + 112 | 71 | — | — |
| T$_B$ (°C.) | 96 | 85 | 115 | 89 | ~115 | 81 | 58 | 61 |
| T$^{RG}$ max (°C.) | 139 | 142 | 168 | 137 | 147 | 127 | 127 | 126 |
| T$^E$ (°C.) | 206 | 238 | 245 | 247 | 241 | 241 | 199 | 206 |
| ΔH$^a$ (kJ) | 72.4 | 103.6 | 81.3 | 101.7$^d$ | 106.3$^d$ | 72.4 | 98.4 | 105.5 |
| Tg (°C.) | — | 162$^b$ | 166$^b$ | 122$^b$ | 113$^b$ | 169$^b$ | 164$^b$ | 168$^b$ |
|  | 166$^c$ | 163$^c$ | 198$^c$ | 162$^c$ | 107$^c$ | 209$^c$ | 208$^c$ | 210$^{c\,e}$ |
| tensile shear strength (N/mm$^2$) | — | 10.0$^b$ | 11.8$^b$ | 14.5$^b$ | 21.9$^b$ | 6.1$^b$ | 3.1$^b$ | 4.5$^b$ |
| (DIN 53,283) | 8.6$^c$ | 9.3$^c$ | 10.5$^c$ | 11.9$^c$ | 22.1$^c$ | 6.0$^c$ | 4.7$^c$ | 2.5$^c$ |

$^a$reaction enthalpy per epoxide equivalent
$^b$curing cycle: pre-gelled for 4 hours at 80° C. and for 8 hours at 140° C.
$^c$curing cycle: pre-gelled for 4 hours at 80° C., for 8 hours at 140° C. and for 6 hours at 180° C.
$^d$extrapolated
$^e$determined by means of TMS (thermomechanical scanning calorimeter)
$^f$on a Mettler TA 3000, heating-up rate 4° C./minute The resistance to chemicals is also determined, as specified in DIN 53,230, on the cured products according to Examples II–VIII. In 5N H$_2$SO$_4$, 5N NaOH, water, acetone and chlorobenzene, the products from Examples II–VIII which have been cured by curing cycle (c) are distinguished throughout by excellent "O" test values. The same applies to the products from Examples II, IV, V and VIII which have been cured by curing cycle (b), while the corresponding, incompletely cured, products from Examples III, VI and VII exhibit somewhat rimetry (DCS) on a Mettler TA 3000

| (25° C.→300° C., 4° C./minute) | T$_1$ | 90° C. |
|---|---|---|
|  | T$_2$ | 171° C. |
|  | T$_3$ | 254° C. |
| single T | 50% | 178.4° C. |
|  | ΔH | 336.2 J/g |
|  | Tg | 196° C. |
| gel time 120° C. (plate) |  | 36' |
| 140° C. |  | 16'30" |
| 160° C. |  | 8'30" |

| | | |
|---|---|---|
| 180° C. | | 4'30" |

EXAMPLE XI

The resin/curing agent mixture described in Example X is cured: (A) for 2 hours at 180° C. and (B) for 4 hours at 200° C. The following properties are determined:

| | A | B |
|---|---|---|
| glass transition temperature DSC | 216 | 217° C. |
| (thermal-mechanical analysis) TMA | 216 | 222° C. |
| (torsional braid analyser) TBA | 206 | 231° C. |
| $1/p^2$ (stiffness) | 0.34 | 0.28 |
| glass transition temperature TBA after storage for 14 days in $H_2O$ at 31° C. | 241 | 246° C. |
| $1/p^2$ (stiffness) | 0.14 | 0.12 |
| % change | −59 | −57 |
| thermogravimetric analysis (TGA) (RT→900° C.) 50% loss in weight | — | 614° C. |
| properties as a lacquer | | |
| Erichsen indentation (DIN 53,156) | 1.8 | 1.3 mm |
| Erichsen impact test | <10 | <10 cm.kg |
| MEK rub test (DIN 53,230) | 0 | 0 |

What is claimed is:

1. A compound of the formula I

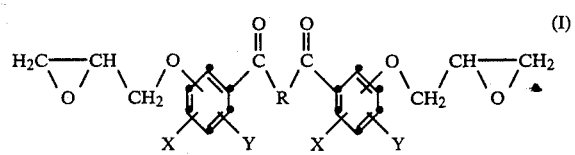

wherein the substituents X independently of one another are hydrogen, alkyl having 1 to 6 C atoms, glycidyloxy or alkoxy having 1 to 6 C atoms, the substituents Y independently of one another are hydrogen or alkyl having 1 to 6 C atoms and R is a direct bond, a group of the formula $-C_mH_{2m}-$, $-C_nH_{2n-2}-$ or $-C_nH_{2n-4}-$ in which m=1–12 and n=2–12, a divalent, saturated or unsaturated cycloaliphatic radical having up to 14 C atoms, a divalent araliphatic radical having up to 14 C atoms, a divalent $C_6-C_{12}$ aromatic radical or a group of the formula II

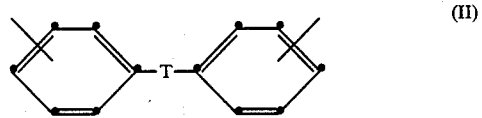

in which T is a direct bond, methylene, isopropylidene, O, S, NH, CO or $SO_2$.

2. A compound of the formula I according to claim 1, wherein the substituents X and the substituents Y are each identical, the substituents X and Y and the glycidyloxy groups are each in the same position relative to the carbonyl group and R is a group of the formula $-C_mH_{2m}-$ in which m=1 to 8, or phenylene.

3. A compound of the formula I according to claim 2, wherein the substituents X are each hydrogen, alkyl having 1 to 4 C atoms or alkoxy having 1 to 4 C atoms and the substituents Y are each hydrogen or alkyl having 1 to 4 C atoms and the glycidyloxy groups are each attached in the para-position relative to the carbonyl groups.

4. A compound of the formula I according to claim 3, wherein the substituents X and Y are in each case identical and are methyl or hydrogen and R is 1,4-phenylene, 1,3-phenylene, 1,4-butylene or 1,8-octylene.

5. A compound of the formula I according to claim 2, wherein the substituents X are each a glycidyloxy group and the substituents Y are each hydrogen or an alkyl group having 1 to 4 C atoms and the glycidyloxy groups are each attached in the ortho-position and the para-position relative to the carbonyl groups.

6. A compound of the formula I according to claim 5, wherein the substituents Y are each hydrogen and R is 1,4-butylene, 1,3-phenylene or 1,4-phenylene.

7. A curable mixture which comprises
   (a) a compound of the formula I according to claim 1, and
   (b) as curing agent a polyamine, a polyphenol, a polycarboxylic acid, a polycarboxylic acid anhydride, or as a compound having catalytic action a tin salt of an alkanoic acid or a Friedel-Crafts catalyst, the amounts of the curing agent employed being such that 0.75 to 1.25 equivalents of amine hydrogen or of phenolic hydroxyl group, or 0.4 to 1.1 equivalents of carboxyl group or anhydride group are used per 1 equivalent of epoxy group, or that 1 to 40 parts by weight of curing agent having catalytic action are used per 100 parts by weight of epoxy resin, and optionally as curing catalyst an effective amount of a tertiary amine, a salt thereof, a quaternary ammonium compound or an alkali metal alcoholate.

8. A compound of the formula I according to claim 1, wherein the glycidyloxy groups are each in the 4'-position, the substituents X and Y are each H and R is a direct bond.

9. A compound of the formula I according to claim 1, wherein the glycidyloxy groups are each in th 4'-position, the substituents X and Y are each H and R is 1,4-phenylene.

10. A compound of the formula I according to claim 1, wherein the glycidyloxy groups are each in the 4'-position, the substituents X and Y are each H and R is 1,3-phenylene.

11. A compound of the formula I according to claim 1, wherein the glycidyloxy groups are each in the 4'-position, the substituents X and Y are each methyl and are in the 3'-position or 5'-position and R is 1,4-phenylene.

12. A compound of the formula I according to claim 1, wherein the glycidyloxy groups are each in the 4'-position, the substituents X and Y are each H and R is 1,4-butylene.

13. A compound of the formula I according to claim 1, wherein the glycidyloxy groups are each in the 4'-position, the substituents X and Y are each H and R is 1,8-octylene.

14. A compound of the formula I according to claim 1, wherein the glycidyloxy groups are each in the 4'-position, the substituents X are each 2'-glycidyloxy, the substituents Y are each H and R is 1,4-phenylene.

15. A compound of the formula I accordng to claim 1, wherein the glycidyloxy groups are each in the 4'-positon, the substituents X are each 2'-glycidyloxy, the substituents Y are each H and R is 1,3-phenylene.

16. A compound of the formula I according to claim 1, wherein the glycidyloxy groups are each in the 4'-position, the substituents X are each 2'-glycidyloxy, the substituents Y are each H and R is 1,4-butylene.

* * * * *